United States Patent
Flagan et al.

(10) Patent No.: US 6,529,272 B2
(45) Date of Patent: Mar. 4, 2003

(54) TECHNIQUES FOR CHARACTERIZING CLOUD CONDENSATION NUCLEL

(75) Inventors: Richard C. Flagan, La Canada (CA); Patrick Yung-Shie Chuang, Santa Cruz, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 09/990,599

(22) Filed: Nov. 20, 2001

(65) Prior Publication Data

US 2002/0046595 A1 Apr. 25, 2002

Related U.S. Application Data

(62) Division of application No. 09/169,247, filed on Oct. 9, 1998, now Pat. No. 6,330,060.
(60) Provisional application No. 60/062,013, filed on Oct. 10, 1997.

(51) Int. Cl.[7] .......................... G01N 15/02; G01N 15/14
(52) U.S. Cl. .................... 356/335; 73/28.01; 250/222.2; 356/37; 374/15
(58) Field of Search ................... 356/37, 335, 336; 250/335, 573, 576, 222.2; 73/25.01, 28.01; 374/15

(56) References Cited

U.S. PATENT DOCUMENTS 2,915,939 A * 12/1959 Van Luck .............. 73/29.05 X
2,953,686 A * 9/1960 Garrison .................... 356/37 X
3,351,759 A * 11/1967 Rich ...................... 73/28.01 X (List continued on next page.)

FOREIGN PATENT DOCUMENTS

JP         57-42839   *  3/1982 ................ 73/865.8

OTHER PUBLICATIONS

Fukuta et al, "The principle of a new horizontal thermal gradient cloud condensation nucleus spectrometer", *Journal de Recherches Atmospheriques*, vol. 13, No. 3, pp. 169–188, Jul.–Sep. 1979.

Fukuta et al, "A Horizontal Thermal Gradient Cloud Condensation Nucleus Spectrometer", *Journal of Applied Meteorology*, vol. 18, No. 10, pp. 1352–1362, Oct. 1979.

Hoppel et al, "Errata", *Journal of Aerosol Science*, vol. 11, No. 4, pp. 421–422, 1980.

Hoppel et al, "A segmented thermal diffusion chamber for continuous measurements of CN", *Journal of Aerosol Science*, vol. 10, No. 4, pp. 369–373, 1979.

Hudson, "An Instantaneous CCN Spectrometer", *Journal of Atmospheric and Oceanic Technology*, vol. 6, No. 6, pp. 1055–1065, Dec. 1989.

Radke et al, "A cloud condensation nucleus spectrometer designed for airborne measurements", *Journal de Recherches Atmospheriques*, vol. 15, No. 3–4, pp. 225–229, Jul.–Dec. 1981.

Hudson et al, "Performance of the continuous flow diffusion chambers", *Journal de Recherches Atmospheriques*, vol. 15, No. 3–4, pp. 321–331, Jul.–Dec. 1981.

*Primary Examiner*—Thomas P. Noland
(74) *Attorney, Agent, or Firm*—Fish & Richardson P.C.

(57) ABSTRACT

A cloud condensation nucleus spectrometer having a streamwise segmented condensation nucleus growth column. The condensation nucleus growth column includes alternating hot and cold temperature-maintaining segments arranged next to one another. The temperature difference between adjacent hot and cold temperature-maintaining segments increases from the input opening to an output opening of the condensation nucleus growth column to produce a supersaturation distribution that increases from the input opening to the output opening.

4 Claims, 4 Drawing Sheets

U.S. PATENT DOCUMENTS

| | | | |
|---|---|---|---|
| 3,462,609 A | * | 8/1969 | Beattie ................... 356/37 X |
| 3,589,169 A | * | 6/1971 | La Fitte et al. ............ 73/25.01 |
| 3,597,084 A | * | 8/1971 | Pagano .................. 73/23.2 X |
| 3,651,686 A | * | 3/1972 | Dizio ..................... 73/25.01 |
| 4,790,650 A | * | 12/1988 | Keady .................. 73/28.01 X |
| 4,902,311 A | * | 2/1990 | Dingfors et al. ............... 55/60 |
| 4,967,095 A | * | 10/1990 | Berger et al. ........ 250/222.2 X |
| 4,967,187 A | * | 10/1990 | Dumas et al. ....... 73/863.01 X |
| 5,026,155 A | * | 6/1991 | Ockovin et al. ............... 356/37 |
| 5,098,657 A | * | 3/1992 | Blackford et al. ........ 356/37 X |
| 5,239,356 A | * | 8/1993 | Höllander et al. ............ 356/37 |
| 5,278,626 A | * | 1/1994 | Poole et al. ............... 356/37 X |
| 5,659,388 A | * | 8/1997 | Scheer et al. .................. 356/37 |
| 5,903,338 A | * | 5/1999 | Mavliev et al. ........... 356/37 X |

* cited by examiner

TECHNIQUES FOR CHARACTERIZING CLOUD CONDENSATION NUCLEI

This application is a divisional application (and claims the benefit of priority under 35 USC 120) of U.S. application Ser. No. 09/169,274, filed Oct. 9, 1998 which is now U.S. Pat. No. 6,330,060 and claims the benefit of U.S. Provisional Application No. 60/062,013, filed Oct. 10, 1997.

ORIGIN OF THE INVENTION

The U.S. Government has certain rights in this invention pursuant to Grant No. N00014-96-1-0119 awarded by the Navy.

FIELD OF THE INVENTION

The present invention relates to aerosol measurements, and more particularly, to instruments and techniques for characterizing cloud condensation nuclei.

BACKGROUND

Atmospheric particles influence the climate system, radiative transfer, visibility, and air quality. Hence, aerosol measurements of concentration, sizes, and chemistry of atmospheric particles are important in many applications, including monitoring air pollution and predicting climate change.

One aspect of aerosol measurements is characterization of cloud condensation nuclei ("CCN"). Under proper humidity conditions, certain aerosol particles are able to nucleate to form cloud droplets. Properties of cloud condensation nuclei provide important information on cloud formation and cloud properties. For example, cloud condensation nuclei can influence the droplet number and size distribution in a cloud, which ultimately affect a variety of processes including cloud lifetime and precipitation rate.

The ability of a particle to nucleate is at least in part determined by the saturation level of the environment, the size of the particle, and the chemical composition of the particle. For example, water vapor is more likely to condense on salt particles such as NaCl than on organic particles. When the relative humidity exceeds the saturation level where the vapor phase and the liquid phase are in equilibrium, a supersaturation state establishes and vapor begins to condense on surfaces and some particles to form droplets or condensation nuclei. At a certain critical supersaturation, when the diameter of a condensation nucleus of a given chemical composition exceeds a critical diameter, the nucleus is said to be "activated", that is, vapor will condense spontaneously on that nucleus and cause the nucleus to grow to a very large size which is limited only by the kinetics of condensational growth and the amount of vapor available for the condensational growth.

The critical diameter at a given supersaturation usually changes with the chemical composition of the particles. Hence, particles of different chemical compositions can become activated at different sizes.

One way to characterize condensation nuclei is to measure the critical supersaturation at which a particle activates. Instruments for such measurements are generally referred to as cloud condensation nucleus counters. Cloud condensation nucleus spectrometers are such counters capable of producing and measuring supersaturations in a desired range. See, for example, Hudson, "An Instantaneous CCN Spectrometer," Journal of Atmospheric and Oceanic Technology, Vol. 6, p. 1055, December, 1989, and Hoppel et al., "A Segmented Thermal Diffusion Chamber for Continuous Measurements of CN," Journal of Aerosol Science, Vol. 10, p. 369, 1979, which are incorporated herein by reference.

The atmospheric environment is usually dynamic. The activation and subsequent growth of could condensation nuclei originated from a subset of atmospheric aerosols are essential to formation of cloud droplets. Therefore, it is desirable to perform in situ measurements in order to accurately measure aerosol samples in real time and monitor the changing climate at a target location. A compact airborne cloud condensation nucleus spectrometer can be used to meet such demand. However, many conventional condensation nucleus spectrometers are ill-suited for small aircraft platforms due to limitations in various factors such as weight, size, time resolution, range of measurable supersaturation.

SUMMARY

The present invention provides a novel CCN spectrometer which has been designed specifically for use on a remotely piloted aircraft for long periods of unattended operation, and which can measure CCN spectra over a wide range of supersaturation at high frequency (one spectrum per minute or faster). The instrument is also designed to be light and consume minimum power in order to conserve the limited resources available on small aircraft.

One embodiment of the CCN spectrometer implements a segmented cloud condensation nucleus growth column. A gas flow channel is formed within the column to receive and transfer a gas flow from an input opening to an output opening and having an inner wall which is wetted by a liquid. The segmented column has a plurality of alternating hot and cold temperature-maintaining segments arranged next to one another relative to the gas flow channel to control and maintain a temperature distribution along the gas flow channel. Each hot temperature-maintaining segment is maintained at a temperature higher than a cold temperature-maintaining segment. The temperatures produce a varying supersaturation environment within the gas flow channel.

In particular, a temperature difference between adjacent hot and cold temperature-maintaining segments increases from the input opening to the output opening to produce a supersaturation distribution that also increases from said input opening to said output opening.

A special optical particle counter is implemented to produce an optical probe beam to illuminate the gas flow in a close proximity to the output opening and to determine presence and dimension of particles in the gas flow.

These and other aspects and advantages of the present invention will become more apparent in light of the accompanying drawings, the detailed description, and the appended claims.

BRIEF DESCRIPTION OF THE DRAWINGS

FIG. 2A shows one embodiment of a segment for the column shown in FIG. 2.

DETAILED DESCRIPTION OF THE PREFERRED EMBODIMENT

Figure 1:
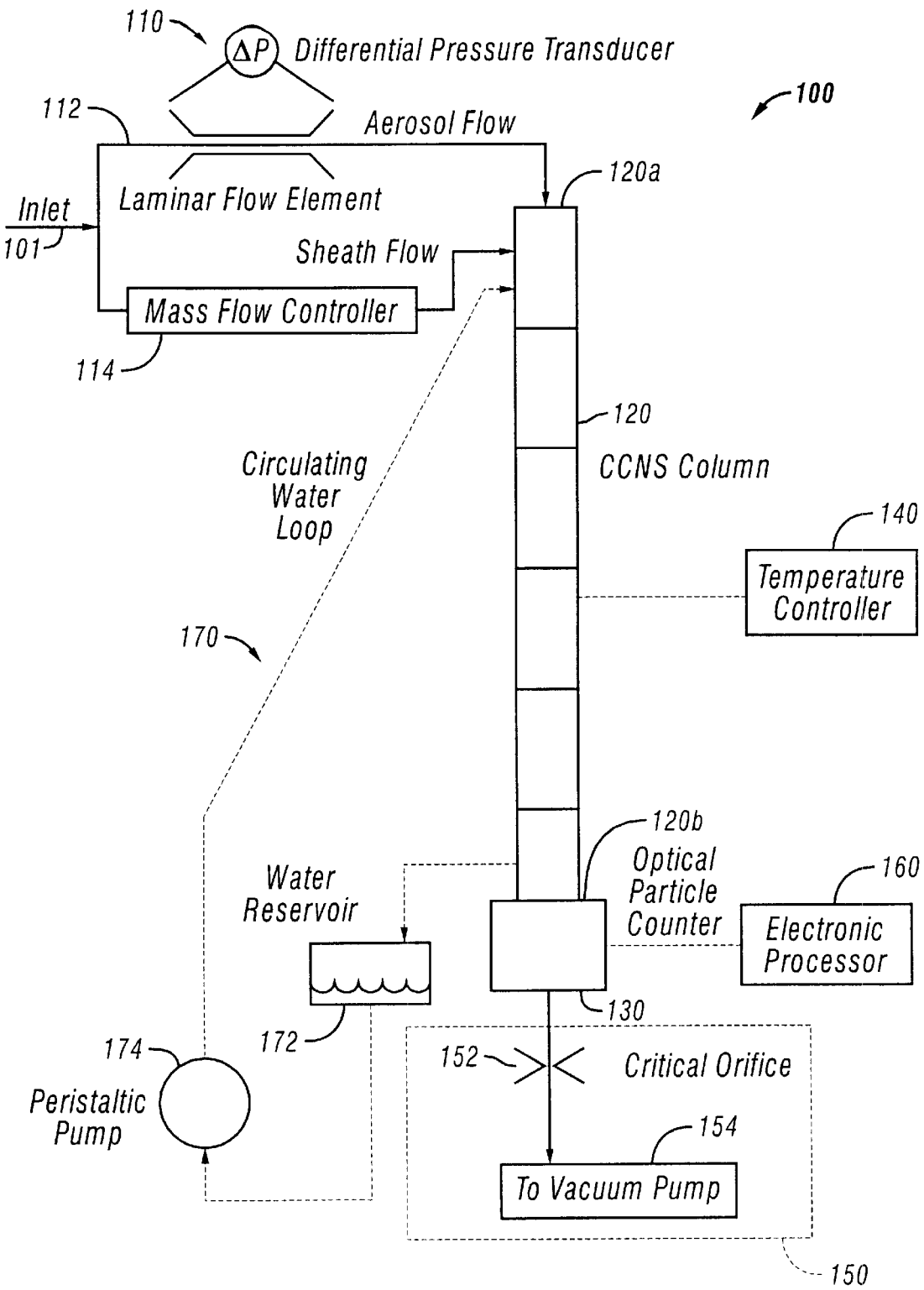
FIG. 1 is a diagram showing one embodiment of a cloud condensation nucleus spectrometer.

FIG. 1 shows one embodiment 100 of a cloud condensation nucleus spectrometer. The spectrometer 100 includes an input flow module 110, a CCN growth column 120, a temperature controller 140 for the CCN growth column 120, and a particle counter 130, an electronic processor 160, and an output flow module 150. The CCN growth column 120 is configured to produce an increasing supersaturation profile from an input end 120A to an output end 120B along the aerosol flow. The aerosol particles having critical supersaturation within the supersaturation range produced by the CCN growth column 120 are activated and exit the CCN growth column 120 with increased sizes.

The particle counter 130 is located at the output end 120B of the condensation column 120 and measures the number of the activated particles in the aerosol flow. Examples of such particle counter includes an optical particle counter which infers particle size from intensity of light scattered from individual particles, and an aerodynamic time-of-flight counter which measures particle size by the particle velocity acquired through rapid acceleration of the gas flow. The electronic processor 160 receives and processes the output signal from the particle counter 130 to produce the respective number of activated particles as a function of the critical supersaturation.

The spectrometer 100 also includes a water supply module 170 having a reservoir 172 to provide water to the CCN growth column 120. Preferably, the CCN growth column 120 may be positioned vertically so that water can be recirculated through the CCN growth column 120 from the top to the bottom by using a single water pump 174. This also minimizes buoyancy induced secondary flows and loss of particles to the column walls by gravitational settlementation. The flow rate of the water may be maintained at a constant low flow rate (e.g., less than 0.5 ml/min).

Figure 2:
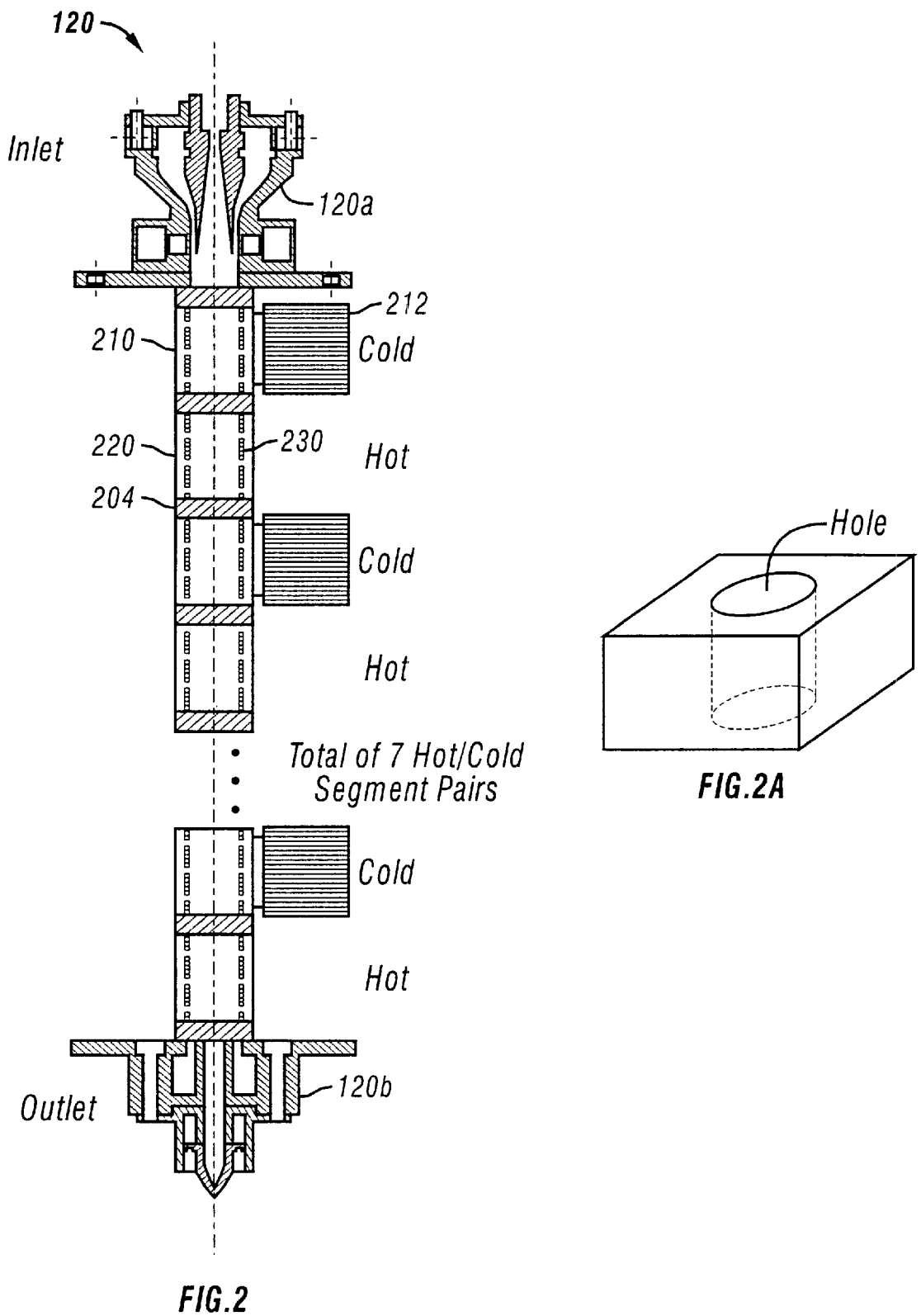
FIG. 2 shows a segmented cloud condensation nucleus column.

The condensation column 120 is preferably divided into a plurality of column segments at different temperatures. FIG. 2 shows the preferred structure of the condensation column 120. Each column segment may be a metal block with a central through hole as shown in FIG. 2A. For example, aluminum block of about 28 mm (H)×25 mm (W)×25 mm (L) with a central hole of about 20 mm in diameter can be used. A thin-walled thermal conductive tube 230 (e.g., formed of stainless steel) may be placed in the center of the condensation column 120 through all column segments to conduct the aerosol flow. Alternatively, the aerosol flow may be conducted by directly using a flow channel formed by the through holes of the column segments. However implemented, the side wall of the flow channel is wetted running the water through the side wall with the water supply module 170. One preferred way of wetting is to line the side wall with filter paper (e.g., Whatman 1 Chr).

The column segments are alternatively maintained at different high and low temperatures which are respectively referred to as "hot" column segments 220 and "cold" column segments 210. Each hot column segment 220 has an electrical heating element (e.g., one or more power resistors) connected to the temperature controller 140 and is maintained at a desired elevated temperature for that segment. A thermal control loop may be implemented to actively control the temperature of each segment. This is well known in the art. Each cold column segment 210 is attached to a cooling element 212, e.g., a thermoelectric cooler, and is maintained at a desired low temperature. A heat sink may be attached to the cooling element 212 to increase the cooling efficiency. At least one thermal sensor (e.g., a thermistor) is disposed in each column segment and connected to the temperature controller 140 to measure the temperature. Adjacent hot and cold column segments 220 and 210 are thermally insulated from each other by a thermal insulation layer 204.

One feature of the condensation column 120 is that the temperature difference between two successive hot and cold column segments increases. One implementation maintains the cold column segments 210 at different temperatures that decrease from the input end 120A to the output end 120B while keeping all hot column segments 220 at a common elevated temperature. Alternatively, the cold column segments 210 may be maintained at a common low temperature and the temperatures of the hot column segments 220 are higher than that low temperature and increase from the input end 120A to the output end 120B. In another variation, neither the cold column segments 210 nor the hot column segments 220 are maintained at a common temperature. However implemented, the temperature profile along the condensation column 120 not only changes in an alternating manner between high and low temperatures from one segment to another but the temperature difference also increases in the hot column segments 220 from the input end 120A to the output end 120B. In the embodiment shown in FIG. 2, the condensation column has a total of seven pairs of cold and hot column segments. The temperature difference between the two segments in each pair can be set at 2° at the beginning and increases 1° per pair. The temperature difference in the last pair at the end 120B is 8°.

This special temperature profile can produce a monotonically increasing supersaturation profile along the center line of the condensation column 120 and can maintain a desired high spatial rate throughout the condensation column 120 without a significant decay near the output end 120B.

The flow rate of the aerosol flow in the condensation column 120 also has a significant impact on the supersaturation profile along the center line of the condensation column 120. When the flow rate is not controlled within a proper range, the supersaturation profile may not be monotonic but may have the same supersaturation at two different positions. The output flow module 150 is used to adjust the flow rate for a given temperature profile in the condensation column 120 to achieve a desired monotonically increasing supersaturation profile.

The input flow module 110 includes an aerosol flow path 112 and a sheath flow 114. The sheath flow 114 is produced by filtering out aerosol particles with a mass flow controller. The relative amount of aerosol versus sheath flow can be controlled by using a mass flow controller 114 (e.g., Sierra Instruments 840). The aerosol flow to the condensation column 120 is the difference between the total input flow 101 and sheath flow 114 and is monitored by measuring the pressure drop across a laminar flow tube in the aerosol flow path 112. The total flow 101 may be controlled by using a critical orifice 152 in the output flow module 150 (e.g., with a nominally flow rate of 0.75 lpm). The output flow module 150 also includes a vacuum pump 154 to induce the aerosol flow.

It should be noted that in this configuration, the instrument is not maintained at a constant pressure. Since the diffusivity of water vapor in air is pressure dependent, this must be accounted for in interpreting the data. Also, since the mass flow controller does not maintain constant volumetric flow rate, rather, the sheath volumetric flow rate increases with decreasing pressure, the relative amounts of aerosol and sheath flow vary with pressure, which also must be accounted for. These flow rates are fed into the electronic processor 160 for data processing.

Figure 3:
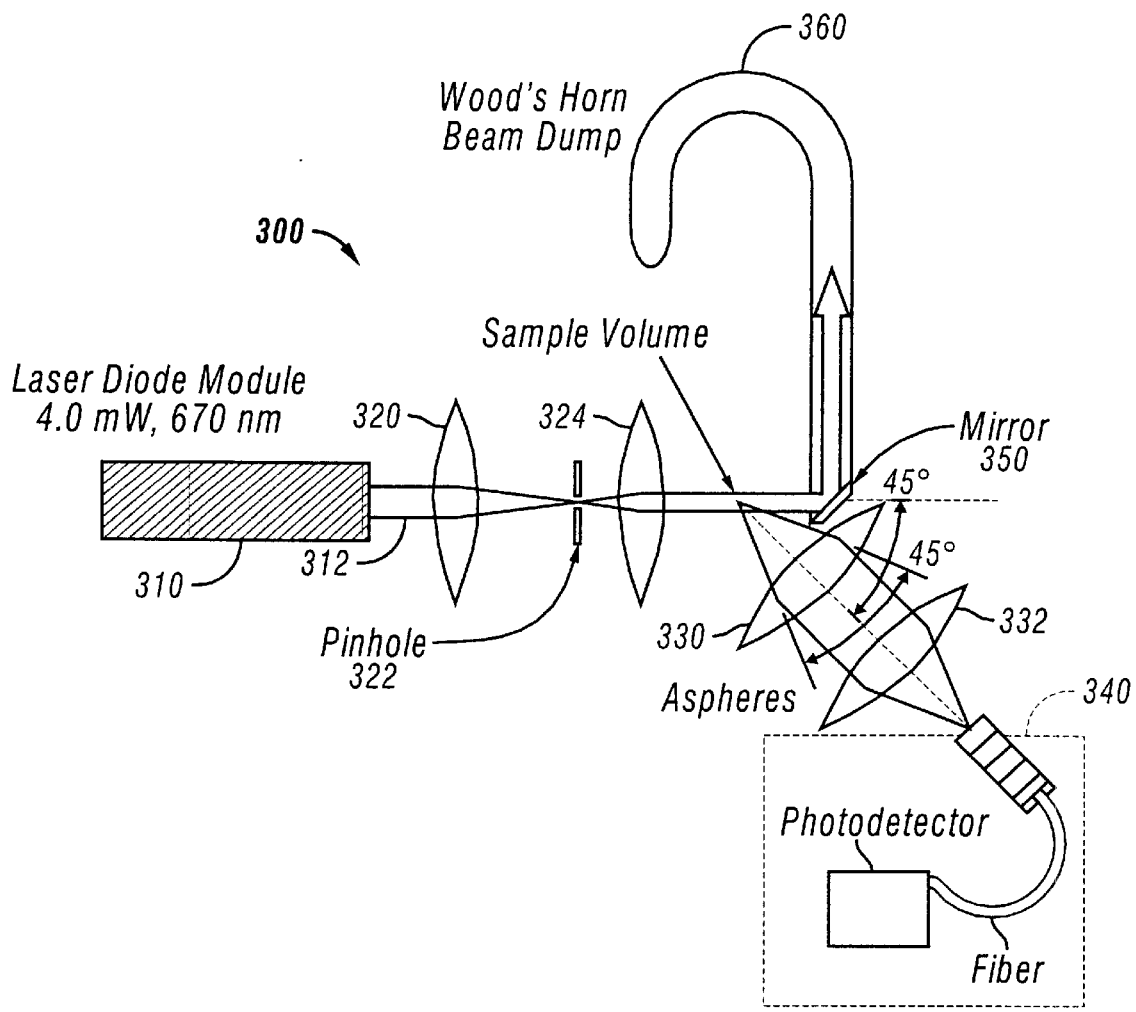
FIG. 3 shows the layout of an optical particle counter integrated to the column of FIG. 2.
Figure 4:
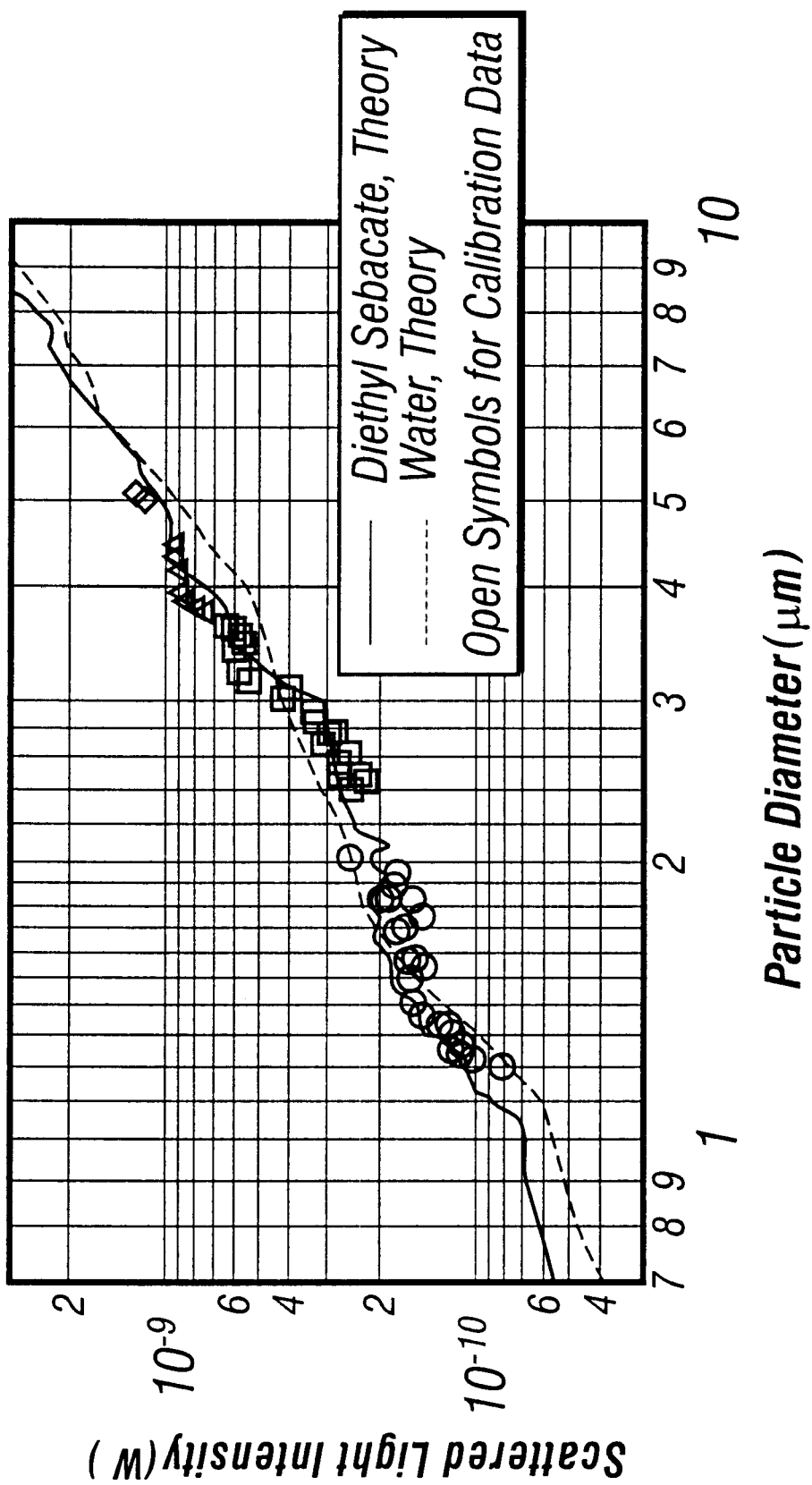
FIG. 4 shows intensity of the scattered light from output aerosol flow as a function of particle size measured by the optical particle counter shown in FIG. 3, where a calculated calibration by using a Diethyl Sebacate flow is also shown.

FIG. 3 shows an optical implementation 300 of the particle counter 130. The aerosol flow is perpendicular to the paper. The optical particle counter 300 is specially designed to improve accuracy in particle counting and to reduce the instrument weight. The optical particle counter 300 is designed for measuring water droplets within a range from about 1 μm to about 20 μm in size. The optical particle counter 300 includes a diode laser 310, a beam collimator formed of lenses 312, 324 and a pinhole 322, an optical collector formed of lenses 330, 332 and a photodetection module 340. The diode laser 310 may be an industrially-packaged laser diode module (e.g., ThorLabs 98002-005) with a line output nominally 1 mm×5 mm wide. The pinhole may be of about 50 μm.

The collimated laser beam from lens 324 is directed to the aerosol flow from the output end 120B of the condensation column 120. The laser beam is preferably perpendicular to the aerosol flow. The dimension of the illuminated region in the aerosol flow is less than the average spacing between two aerosol particles so that, on the average, only a single particle is illuminated by the laser beam. This substantially reduces the probability of two droplets passing through the beam simultaneously while maximizing the uniformity of the intensity see by particles passing through slightly different parts of the beam. The beam is spatially-filtered by the pinhole 322 because spurious uncollimated light can introduce an excessively high background light level. A particle is counted when a strong optical signal caused by scattering from a particle is detected by the photodetection module 340.

In general, the output nozzle of the output end 120B is as small as possible so that the CCN droplets all pass through the same part of the laser beam. However, it has been found that tip diameters significantly smaller than 1 mm may cause droplet impaction. Preferably, a nozzle with a half angle of about 15° and an output diameter of about 1 mm may be used. Other means of directing the grown particles exiting the growth column to the view volume may also be used. A mirror 350 and a beam dump 360 may be implemented to guide the main laser beam away from the lens 330 to reduce the background noise.

Collection lenses 330 and 332 are positioned relative to the intersection point 326 of the laser beam and the aerosol flow so that the scattered light is collected at a direction of about 45° off the propagation direction of the laser beam. The lens 330 has a solid collection angle of about 45°. Two aspheric lenses may be used as the lenses 330 and 332. The direction of detection and the solid collection angle of the lens 330 should be properly selected to ensure a monotonic dependence of the intensity of the collected light and the particle size.

The photodetection module 340 may include a fibre optic patch cord (e.g., 1 mm core) to receive and transmit the light to a photodetector such as a photomultiplier tube or a photodiode (e.g., an avalanche photodiode detector). A multichannel analyzer (e.g., EG\&G Ortec Trump-2k) card may be included in the electronic processor 160 to measure the peak height of the pulses, each of which represents one droplet.

FIG. 4 shows a calculated response of the optical particle counter and measured calibration data using droplets of a clear, non-volatile organic liquid, diethyl sebacate (n=1.436), generated from a Berglund-Liu vibrating orifice aerosol generator.

The optical particle counter 300 of FIG. 3 can be integrated to the condensation column 120 so that the laser probe beam intersects with the output aerosol flow at a location close to the output end 120B. Since water droplets are volatile and water condensed on an aerosol particle can vaporize after leaving the condensation column 120, it is critical to measure the particles at a location as close to the output end 120B as possible. Many conventional particle counters including optical counters often introduce the output aerosol flow into a flow path before measurements and can significantly degrade the accuracy of the measurements. Implementation of the optical particle counter 300 can essentially eliminate the additional flow path outside the output end 120B and improves the accuracy of measurements.

The above design can be used to significantly reduce the weight (e.g., less than 35 pounds) and size of a CCN spectrometer and thereby reduce the power consumption (e.g., about 100 W) and requirements of the power supply (e.g., a 28-V source). The on-board electronic processor further allows for automatic operation without human intervention.

Although the present invention has been described in detail with reference to the preferred embodiments, various modifications and enhancements may be made without departing from the appended claims.

What is claimed is:

1. A method, comprising:

directing a gas flow into a gas flow channel from an input opening to an output opening;

vaporizing a liquid to produce a vapor from the liquid to fill the gas flow channel;

producing a spatial temperature distribution in the gas flow channel that changes with position from the input opening to the output opening, and that includes a plurality of alternating hot and cold regions arranged next to one another where a hot region has a temperature higher than an adjacent cold region;

selecting temperatures of the hot and cold regions to spatially increase a temperature difference between adjacent hot and cold segments from the input opening to the output opening in the gas flow channel; and determining presence and dimension of particles in the gas flow which are condensed with the vapor.

2. The method as in claim 1, wherein the hot regions in the gas flow channel are maintained at a constant elevated temperature and the cold regions are maintained at different temperatures which monotonically decrease from the input opening to the output opening and are lower than the elevated temperature.

3. The method as in claim 1, wherein the cold regions are maintained at a constant low temperature and the hot regions are maintained at different temperatures which increase with position from the input opening to the output opening and are higher than the low temperature.

4. The method as in claim 1, wherein the presence and dimension of particles in the gas flow are measured optically by illuminating an optical beam to the gas flow at the output opening, without introducing another flow into the gas flow.

* * * * *